United States Patent [19]

James et al.

[11] Patent Number: 5,456,911
[45] Date of Patent: Oct. 10, 1995

[54] SYNTHETIC MALARIAL ANTIGENS AND USES THEREOF

[75] Inventors: Mark A. James; Sonia Montenegro-James, both of New Orleans, La.

[73] Assignee: The Administrators of the Tulane Educational Fund, New Orleans, La.

[21] Appl. No.: 3,966

[22] Filed: Jan. 15, 1993

[51] Int. Cl.$^6$ ..................... A61K 39/015; A61K 38/08; A61K 38/16
[52] U.S. Cl. ..................... 424/191.1; 424/185.1; 424/265.1; 424/268.1; 424/272.1; 530/324; 530/325; 530/326; 530/327; 530/328; 530/329
[58] Field of Search ................... 424/88, 268.1, 424/191.1, 185.1, 272.1; 530/326–329, 324, 325

[56] References Cited

U.S. PATENT DOCUMENTS 4,554,101  10/1985  Hopp ........................................ 530/324

OTHER PUBLICATIONS

Butcher et al. Parasitology 98:315–327 1989.
Cox et al. TIBTECH 9:390–393 1991.
Pongor et al. Methods in Enzymology 154: 450–473 1987.
Baird et al., "GE–Dependent Acquired Protection Against *Plasmodium Falciparum* in People Having Two Years Exposure to Hyperendemic Malaria," *Am. J. Trop. Med. Hyg.*, 45(1):65–76, 1991, published in USA.
Bate et al., "Malaria Exoantigens Induce T–Independent Antibody that Blocks Their Ability to Induce TNF," *Immunology*, 70:315–320, 1990, published in Europe.
Berzofsky, Jay A., "Mechanisms of T Cell Recognition with Application to Vaccine Design," *Molecular Immunology*, 28(3):217–223, 1991, published in Europe.
Braun–Breton, "In Vivo Time Course of Synthesis and Processing of Major Schizont Membrane Polypeptides in *Plasmodium Falciparum*," *Molecular and Biochemical Parasitology*, 20:33–43, 1986, published in Europe.
Briand et al., "Synthetic Peptides as Antigens: Pitfalls of Conjugation Methods," *Journal of Immunological Methods*, 78:59–69, 1985, published in Europe.
Campbell et al., "Use of Synthetic and Recombinant Peptides in the Study of Host–Parasite Interactions in the Malarias," *Am. J. Trop. Med. Hyg.*, 37(3):428–444, 1987, published in USA.
Chiodina and Moody, "Techniques for the Detection of Malaria Parasites," *Journal of the Royal Society of Medicine*, 82(17):41–43, 1989, published in Europe.
Chizzolini et al., "Natural Antibodies Against Three Distinct and Defined Antigens of *Plasmodium Falciparum* in Residents of a Mesoendemic Area in Gabon," *Am. J. Trop. Med. Hyg.*, 39(2):150–156, 1988, published in USA.
Chou and Fasman, "Prediction of Protein Conformation," *Biochemistry*, 13(2):222–245, 1974, published in USA.
Deloron et al., "Antibodies to *Plasmodium Falciparum* Ring–Infected Erythrocyte Surface Antigen and *P. Falciparum* and *P. Malariae* Circumsporozoite Proteins: Seasonal Prevalance in Kenyan Villages," *Am. J. Trop. Med. Hyg.*, 41(4):395–399, 1989, published in USA.
Good and Miller, "T–Cell Antigens and Epitopes in Malaria Vaccine Design," *Current Topics in Microbiology and Immunology*, 155:65–78, 1990, published in Europe.
Grau et al., "Tumor Necrosis Factor and Disease Severity in Children with Falciparum Malaria," *The New England Journal of Medicine*, 320:1586–1591, 1989, published in USA.
Hopp and Woods, "Prediction of Protein Antigenic Determinants from Amino Acid Sequences," *Proc. Natl. Acad. Sci. USA*, 78(6):3824–3828, 1981, published in USA.
James et al., "Induction of Protective Immunity to *Plasmodium falciparum* in *Saimiri sciureus* Monkeys with Partially Purified Exoantigens," *Infection and Immunity*, 49(3):476–480, 1985, published in USA.
Karunaweera et al., "Dynamics of Fever and Serum Levels of Tumor Necrosis Factor are Closely Associated During Clinical Paroxysms in *Plasmodium vivax* Malaria," *Proc. Natl. Acad. Sci. USA*, 89:3200–3203, 1992, published in USA.
Kwiatkowski et al., "Tumour Necrosis Factor Production in Falciparum Malaria and Its Associated with Schizont Rupture," *Clin. Exp. Immunol.*, 77:361–366, 1989, published in Europe.
Kwiatkowski et al., "TNF Concentration in Fatal Cerebral, Non–Fatal Cerebral, and Uncomplicated *Plasmodium falciparum* Malaria," *The Lancet*, 336:1201–1204, published in Europe.

(List continued on next page.)

*Primary Examiner*—Christine M. Nucker
*Assistant Examiner*—Anthony C. Caputa
*Attorney, Agent, or Firm*—Arnold, White & Durkee

[57] ABSTRACT

The present invention includes novel peptides GQDE-GEENEG, SEQ. ID NO:1 GRNGLGANTDQDDQLEDE, SEQ. ID NO:2 DQFFDANPNLFQLLEPVEFDED, SEQ. ID NO:3 and LVFLVQQPFLFVLWDQNEKF-PVFMGVYDP SEQ. ID NO:3. Such peptides are useful for detecting antibodies against circulating malarial antigens. In one aspect, these peptides may be copolymerized or crosslinked to form immunogens presenting epitopes of the malarial *Plasmodium falciparum* antigen Pf70. Preferably at least two of the above peptides are so crosslinked. Most preferably, all four peptides are copolymerized. The crosslinking agent preferred is glutaraldehyde although, of course, other crosslinking agents such as dialdehydes of various lengths, for example, or even possibly the carbodiimides may be used. Compositions of matter comprising such peptides in crosslinked or copolymerized forms are an important part of the present invention, particularly when used as immunogens. Rabbits have been immunized with a composition of the four crosslinked peptides at a dose of 2.5 mg (administered three times). An analogous dose for larger animals should, of course, produce the same response to induce immunity to malaria. The present invention also, of course, includes a method of producing an antigen usable to generate antibodies reacting with malarial organisms, *Plasmodium falciparum* and *Plasmodium vivax*. The above copolymerizing methodology utilizing crosslinking agents with the peptides of choice is the method of production.

4 Claims, 7 Drawing Sheets

OTHER PUBLICATIONS

Kyte and Doolittle, "A Simple Method for Displaying the Hydropathic Character of a Protein," *J. Mol. Biol.*, 157:105–132, 1982, published in Europe.

Leclerc et al., "A Synthetic Vaccine Constructed by Copolymerization of B and T Cell Determinants," *Eur. J. Immunol.*, 17:269–273, 1987, published in Europe.

Mendis, K. N., "Contrasting Clinical Disease in *Plasmodium vivax* and *Plasmodium falciparum* Malaria, and the Association of both with Cytokines," *Bull. Inst. Pasteur*, 90:3–9, 1992, published in Europe.

Merrifield, R. B., "Solid Phase Peptide Synthesis. I. The Synthesis of a Tetrapeptide," *JACS*, 85:2149–2154, 1963, published in USA.

Molyneux, M. E., "Cerebral Malaria in Children: Clinical Implications of Cytoadherence," *Am. J. Trop. Med. Hyg.*, 43(2):38–41, 1990, published in USA.

Petersen et al., "An Epidemiological Study of Humoral and Cell–Mediated Immune Response to the *Plasmodium Falciparum* Antigen PF155/RESA in Adult Liberians," *Am. J. Trop. Med. Hyg.*, 41(4):386–394, 1989, published in USA.

Playfair et al., "Don't Kill the Parasite: Control the Disease," *Acta Leidensia*, 60(1):157–165, 1991, published in Europe.

Playfair et al., "The Malaria Vaccine: Anti–Parasite or Anti–Disease?" *Immunology Today*, 11(1):25–27, 1990, published in Europe.

Daniel–Ribeiro et al., "Study of the Humoral Response Against Three Defined *P. Falciparum* Antigens in Different Populations Using Synthetic Peptides and an Immunoenzymatic Assay," *IV International Congress on Malaria and Babesiosis*, Abstract No. 2.22, 1991, published in South America.

Scuderi et al., "Raised Serum Levels of Tumour Necrosis Factor in Parasitic Infections," *The Lancet*, pp. 1364–1365, 1986, published in Europe.

Shamansky, L. M., "Purification and Characterization of Soluble Antigens from the Human Malaria Parasite, Plasmodium Falciparum," Thesis, The University of Illinois at Urbana–Champaign, 1986, printed in USA.

Shamansky et al., "Purification and Characterization of Culture–Derived Exoantigens of *Plasmodium Falciparum*," *Molecular and Biochemical Parasitology*, 17:299–310, 1985, published in Europe.

Stone et al., "Enzymatic Digestion of Proteins and HPLC Peptide Isolation," *A Practical Guide to Protein and Peptide Purification for Microsequencing*, Academic Press, Inc., pp. 31–34, 37–42, 44–47, and 119, 1989, published in USA.

Stone et al., "Reversed–Phase High–Performance Liquid Chromatography for Fractionation of Enzymatic Digests and Chemical Cleavage Products of Proteins," *Methods in Enzymology*, 193:389–412, 1990, published in USA.

Tapchaisri et al., "Antibodies Against Malaria Sporozoites in Patients with Acute Uncomplicated Malaria and Patients with Cerebral Malaria," *Am. J. Trop. Med. Hyg.*, 34(5):831–836, 1985, published in USA.

Taverne et al., "Two Soluble Antigens of *Plasmodium falciparum* Induce Tumor Necrosis Factor Release from Macrophages," *Infection and Immunity*, 58(9):2923–2928, 1990, published in USA.

Taverne et al., "Human and Murine Macrophages Produce TNF in Response to Soluble Antigens of *Plasmodium falciparum*," *Parasite Immunology*, 12:33–34, 1990, published in Europe.

Thelu et al., "Purification and Immunochemical Study of *Plasmodium Falciparum* Exoantigens," *J. Parasit.*, 71(5):542–546, 1985, published in USA.

Trager and Jensen, "Human Malaria Parasites in Continuous Culture," *Science*, 193:673–675, 1976, published in USA.

WHO Scientific Group, "The Use of Synthetic Antigens for Diagnosis of Infectious Diseases," *WHO. Tech. Rep. Ser.*, 784–59–64, 1989, place of publication unknown.

Wilson et al., "Antigens Associated with *Plasmodium Falciparum* Infections in Man," *The Lancet*, pp. 201–205, 1969, published in Europe.

Chizzolini et al., "Age–Related Prevalence of Antibody Response Against Three Different, Defined *Plasmodium falciparum* Antigens in Children from the Haut–Ogooué Province in Gabon," *Transactions of the Royal Society of Tropical Medicine and Hygiene*, 83:147–151, 1989, published in Europe.

Deloron and Cot, "Antibodies to the Ring–Infected Erythrocyte Surface Antigen and the Circumsporozoite Protein of *Plasmodium falciparum* in a Rural Community from Burkina Faso," *Transactions of the Royal Society of Tropical Medicine and Hygiene*, 84:191–195, 1990, published by Europe.

Esposito et al., "Prevalence and Levels of Antibodies to the Circumsporozoite Protein of *Plasmodium falciparum* in an Endemic Area and Their Relationship to Resistance Against Malaria Infection," *Transactions of the Royal Society of Tropical Medicine and Hygiene*, 82:827–832, 1988, published in Europe.

Mendis et al., "Anti–Circumsporozoite Protein Antibodies Measure Age Related Exposure to Malaria in Kataragama, Sri Lanka," *Parasite Immunology*, 14:75–86, 1992, published in Europe.

Rosenberg and Wirtz, "Intrinsic Individual Differences in Circumsporozoite Antibody Repsonse at a Hyperendemic Malaria Focus," *Transactions of the Royal Society of Tropical Medicine and Hygiene*, 84:206–208, 1990, published in Europe.

Sanchez et al., "Malaria in the Amazon. Prevalence of *Plasmodium falciparum* Antibodies in Amerindians Inhabiting the Venezuelan Amazon," *Annals of Tropical Medicine and Parasitology*, 84(4);307–312, 1990, published in Europe.

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 10 amino acid residues
        ( B ) TYPE: amino acid
        ( D ) TOPOLOGY: linear ( x i ) SEQUENCE DESCRIPTION: SEQ ID NO:1:

Gly Gln Asp Glu Gly Glu Glu Asn Glu Gly
1               5                   10

( 2 ) INFORMATION FOR SEQ ID NO:2:

( i ) SEQUENCE CHARACTERISTICS:
        ( A ) LENGTH: 18 amino acid residues
        ( B ) TYPE: amino acid
        ( D ) TOPOLOGY: linear ( x i ) SEQUENCE DESCRIPTION: SEQ ID NO:2:

Gly Arg Asn Gly Leu Gly Ala Asn Thr Asp Gln Asp Asp Gln Leu Glu
1               5                   10                  15
Asp Glu ( 2 ) INFORMATION FOR SEQ ID NO:3:

( i ) SEQUENCE CHARACTERISTICS:
        ( A ) LENGTH: 22 amino acid residues
        ( B ) TYPE: amino acid
        ( D ) TOPOLOGY: linear ( x i ) SEQUENCE DESCRIPTION: SEQ ID NO:3:

Asp Gln Phe Phe Asp Ala Asn Pro Asn Leu Phe Gln Leu Leu Glu Pro
1               5                   10                  15
Val Glu Phe Asp Glu Asp
                20

( 2 ) INFORMATION FOR SEQ ID NO:4:

( i ) SEQUENCE CHARACTERISTICS:
        ( A ) LENGTH: 29 amino acid residues
        ( B ) TYPE: amino acid
        ( D ) TOPOLOGY: linear ( x i ) SEQUENCE DESCRIPTION: SEQ ID NO:4:

Leu Val Phe Leu Val Gln Gln Pro Phe Leu Phe Val Leu Trp Asp Gln
1               5                   10                  15
Asn Glu Lys Phe Pro Val Phe Met Gly Val Tyr Asp Pro
                20                  25

SYNTHETIC MALARIAL ANTIGENS AND USES THEREOF

The U.S. government has rights in the present invention related to support by Grant No. DHR-5600-G-00-1044-00 Program in Science and Technology Cooperation, Office of the Science Advisor, U.S. Agency for International Development.

BACKGROUND OF THE INVENTION

Many of the malarial asexual blood-stage antigens thus far identified are associated with cytoplasmic inclusions and/or accumulate within the parasitophorous vacuole of the infected erythrocyte. Such antigens may be shed or secreted into the plasma of infected individuals or into the supernatant medium of in vitro cultures, especially upon schizont rupture. These soluble antigens have been historically referred to as exoantigens (Wilson et el. 1969). Since exoantigens are known to occur in the circulation of patients with malaria, they may be responsible for excess production of tumor necrosis factor (TNF), a mediator that is thought to play a central role in the pathogenesis of the disease (Scuderi et el. 1986; Kwiatkowski et al. 1989, 1990; Taverne et al. 1990a,b; Playfair et al. 1991; Mendis 1992). TNF may promote cytoadherence and sequestration of *Plasmodium falciparum*-infected erythrocytes (Grau et al. 1989; Molyneux 1990) and when produced in excessive levels may predispose to cerebral malaria and a fatal outcome (Kwiatkowski et al. 1990). In addition, malarial fevers as a result of *P. falciparum* and *P. vivax* infections may be mediated, at least in part, through paroxysmal TNF release associated with schizont rupture (Kwiatkowski et el. 1989; Karunaweera et al. 1992; Mendis 1992). It has been suggested that immunization with an exoantigen(s) might provide a means of protection against the clinical effects of malaria and of generating anti-disease immunity by reducing cytokine production (Bate et el. 1990; Playfair et el. 1990). Such an exoantigen-based, anti-disease vaccine would minimize the clinical manifestations of *P. falciparum* malaria, thereby extending life until the development of solid naturally-acquired immunity.

The present invention relates to the immunogenicity and antigenicity of novel peptides and a unique synthetic peptide hybrid (SPf70) derived from internal chymotryptic fragments of a major 70 kDa *P. falciparum* (Indochina I/CDC) schizont protein (Shamansky et al. 1985; Braun-Breton et al. 1986). It has been suggested that the 70 kDa polypeptide is a degradation product of a 120 kDa schizont membrane protein, with the 70 kDa protein increasing in amount at the time of merozoite release/reinvasion (Braun-Breton et al. 1986). This antigen was selected for study because of its immunogenicity and efficacy in inducing partial protective immunity in susceptible Bolivian Saimiri monkeys (James et al. 1985). Partially purified (enriched for the 70 kDa antigen) supernatant fluids of *P. falciparum* Indochina I and Geneve/SGE-1 strains conferred significant clinical protection of squirrel monkeys against challenge with the homologous Indochina I strain and a moderate degree of heterologous strain immunity. Subsequently, monospecific rabbit antibodies to the 70 kDa polypeptide were shown to have schizont specificity by immunofluorescence, and approximately 50% inhibition of *P. falciparum* growth after 72 h of in vitro culture.

Synthetic peptides have been shown to be powerful tools for the seroepidemiology and diagnosis of malaria (WHO Scientific Group, 1989). From the standpoint of immunodiagnosis, it is desirable to utilize peptides that are both specific and conserved between different parasite strains (Chizzoline et al., 1989; Peterson et al., 1989). Using defined antigens various seroepidemipologic surveys have shown that in malaria-endemic areas, antibodies to selected parasite proteins, such as the circumsporozoite (CS) protein, Pf155/RESA and MSA-1, increase with age and exposure to malaria parasites (Campbell et al., 1987; Chizzolini et al., 1988; Petersen et al., 1989). However, reports have indicated that individuals in endemic regions, at equal risk for malaria, show intrinsic differences in their ability to generate antibodies against specific parasite proteins (Chizzolini et al., 1988; Rosenberg and Wirtz, 1990). Synthetic peptides have been of value in monitoring antibody levels in areas where malaria transmission is seasonal and/or unstable (Esposito et al., 1988; Deloron et al., 1989; Deloron and Cot, 1990). In general, such studies have shown that antibodies to blood-stage parasites do not persist in the absence of reexposure. (Tapchaisri et al., 1985; Wijesundera et al., 1990.)

SUMMARY OF THE INVENTION

The present invention includes novel peptides GQDEGEENEG, SEQ ID NO:1 GRNGLGANTDQDDQLEDE, SEQ ID NO:2 DQFFDANPNLFQLLEPVEFDED, SEQ ID NO:3 and LVFLVQQPFLFVLWDQNEKFPVFMGVYDP SEQ ID NO:4. Such peptides are useful for detecting antibodies against circulating malarial plasmodia antigens.

In one aspect, these peptides may be copolymerized or crosslinked to form immunogens presenting epitopes of the malarial *Plasmodium falciparum* antigen Pf70. Preferably at least two of the above peptides are so crosslinked. Most preferably, all four peptides are copolymerized. The crosslinking agent preferred is glutaraldehyde although, of course, other crosslinking agents such as dialdehydes of various lengths, for example, or even possibly the carbodiimides may be used. Compositions of matter comprising such peptides in crosslinked or copolymerized forms are an important part of the present invention, particularly when used as immunogens. Rabbits have been immunized with a composition of the four crosslinked peptides at a dose of 2.5 mg (administered three times). An analogous dose for larger animals should, of course, produce the same response to induce immunity to malaria. The present invention also, of course, includes a method of producing an antigen usable to generate antibodies reacting with malarial organisms, *Plasmodium falciparum* and *Plasmodium vivax*. The above copolymerizing methodology utilizing crosslinking agents with the peptides of choice is the method of production.

In another aspect of the present invention, an assay is claimed for detecting the presence of antibodies reactive with circulating malarial antigens in a biological sample. The biological sample may be human serum or plasma. The immunoassay comprises the steps of affixing to a surface a mixture consisting essentially of at least one of the following peptides: GQDEGEENEG, SEQ ID NO:1 GRNGLGANTDQDDQLEDE, SEQ ID NO:2 DQFFDANPNLFQLLEPVEFDED, SEQ ID NO:3 or LVFLVQQPFLFVLWDQNEKFPVFMGVYDP SEQ ID NO:4. A mixture consisting essentially of at least one of the listed peptides means that one peptide may be used or more than one peptide may be used. The peptide mixture may be crosslinked and attached to a surface. The next step is to incubate the affixed peptides with a quantity of the biological sample to permit binding of reactive antibodies with the affixed peptides to form a bound product. The presence of antibodies reactive with circulating malarial antigens is determined by contacting the bound product with indicator antibodies. The indicator antibodies may be an enzyme linked antibody, a fluorescent tagged antibody, or a radiolabeled antibody.

A further embodiment of the present invention is an assay for detecting the presence of circulating malarial antigens in a biological sample. The biological sample may be human serum or human plasma. The first step of this assay is the preparation of antibodies by steps comprising administering to an animal antigenically effective amounts of an antigen consisting essentially of crosslinked peptides GQDE-GEENEG, SEQ ID NO:1 GRNGLGANTDQDDQLEDE, SEQ ID NO:2 DQFFDANPNLFQLLEPVEFDED, SEQ ID NO:3 or LVFLVQQPFLFVLWDQNEKFPVFMGVYDP SEQ ID NO:4; the next step is to affix to a surface the prepared antibodies to form affixed antibodies. The next step is to incubate the affixed antibodies with a quantity of the biological sample to permit binding of malarial antigens with the affixed antibodies to form a bound product. The presence of circulating malarial antigens bound to affixed antibodies is determined by contacting the bound product with an indicator antibody binding the circulating malarial antigens bound to affixed antibodies. The indicator antibody may be an enzyme linked antibody, a fluorescent tagged antibody, or a radiolabeled antibody.

BRIEF DESCRIPTION OF THE DRAWINGS

FIG. 1A depicts reactivity of individual peptides (C2, C3, C5, C10) and the peptide complex (PC) to antibodies in serially diluted antisera. Fig. 1B shows antibody reactivity in a competitive inhibition ELISA after preincubation with homologous peptides.

DETAILED DESCRIPTION OF PREFERRED EMBODIMENTS

Figure 1A:
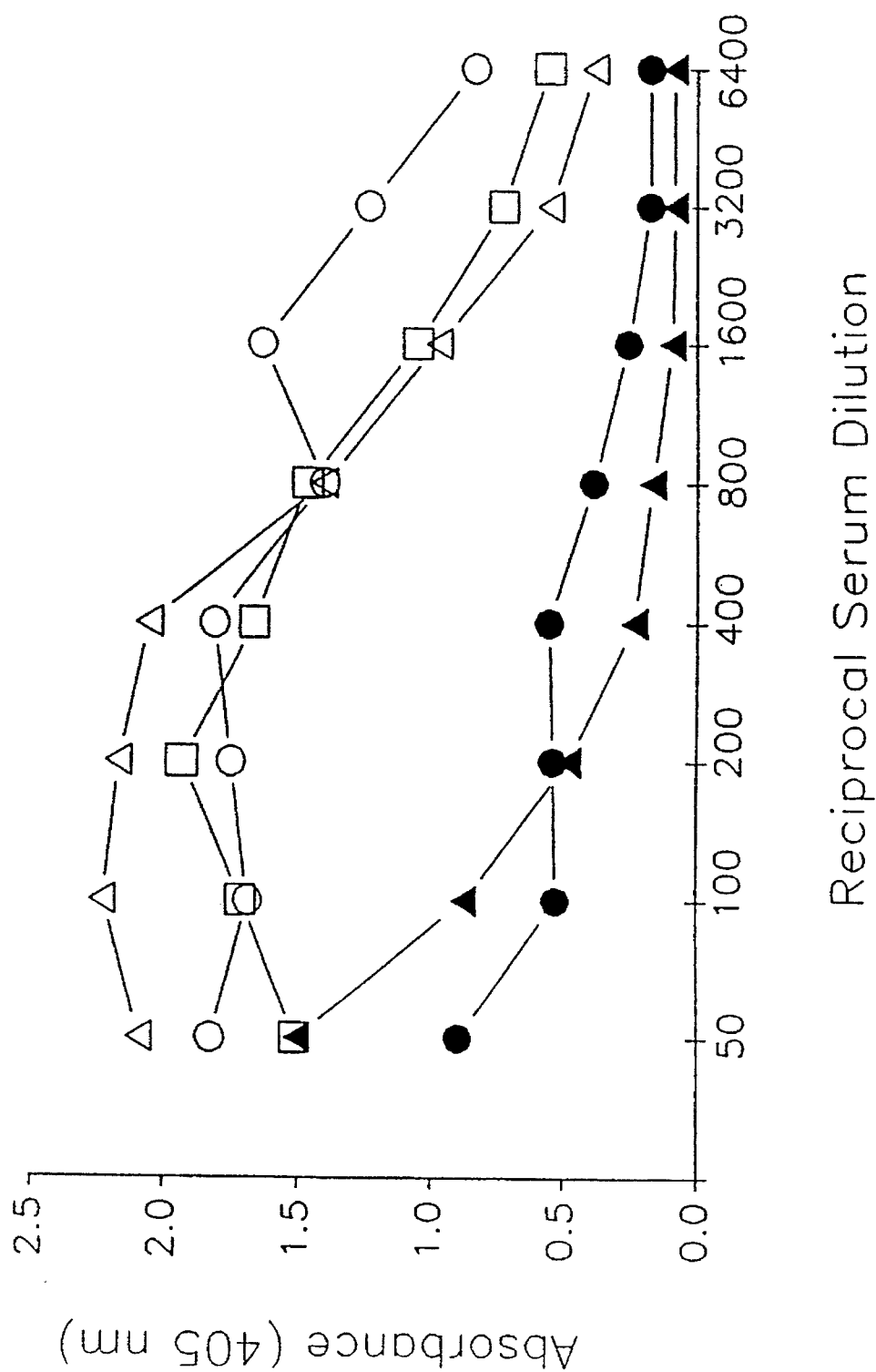
FIGS. 1A and 1B concern the immunogenicity of the synthetic peptide complex SPf70. Rabbit antibody responses to the peptide complex were measured by ELISA.

A 70kDa *Plasmodium falciparum* exoantigen (Pf70) was purified from supernatant fluids of continuous in vitro *P. falciparum* cultures using sequential cation-exchange and high performance liquid chromatographic procedures. The purified protein was then digested with chymotrypsin and amino acid sequences determined for the resulting fragments. Four peptides (termed C2, C3, C5, C10) were subsequently selected for synthesis, based on their predictability for antigenic sites. The individual peptides are usable to detect the presence of antibodies directed toward antigens of malarial organisms. The peptides were effectively used as a synthetic immunogen (SPf70) when crosslinked (copolymerized) with glutaraldehyde in the absence of a carrier. The synthetic peptide complex, when administered with Freund's adjuvant, was found to be highly immunogenic in rabbits. Serologic reactivity to the peptide complex and peptides C2 and C5 was uniformly high, followed by the responses to C3 and C10. Peptide antigenicity was also assessed with human anti-*P. falciparum* sera from malaria-endemic regions of Uganda and Venezuela. ELISA data showed that anti-*P. falciparum* antibodies were specific for and reactive to the peptides. The specificity of the rabbit anti-SPf70 antibodies for *P. falciparum* antigen was shown by immunoprecipitation of metabolically labelled proteins and by immunoblotting. Herein are described peptide sequences of a 70 kDa *P. falciparum* exoantigen (Pf70), that when synthesized and constructed as a copolymer (SPf70), are able to induce the formation of antibodies that are reactive with the native malarial protein. The high immunogenicity and antigenic reactivity of SPf70 indicate the potential use of this synthetic peptide polymer as an immunogen and diagnostic reagent.

Indirect fluorescent antibody (IFA) tests and enzyme-linked immunosorbent assays (ELISA) were used to measure antibodies to *Plasmodium falciparum* in patients with acute malaria from Bolivar State, Venezuela. Antibody titers increased significantly with repeated malarial episodes. IgG antibody responses to 4 synthetic peptides (termed C2, C3, C5, C10) derived from a 70 kDa *P. falciparum* (Indochina I/CDC strain) exoantigen were evaluated by a peptide-ELISA with overall positivity rates of 20%, 40%, 20% and 58%, respectively. Seropositivity to peptide C10 was consistently over 50% (range 53–75%) among patients of different ages. Overall IgM reactivity to the respective peptides was 53%, 30%, 83% and 70%. IgM reactivity was generally greater in patients with primary malarial infections. The ELISA is a useful adjunct to the IFA in measuring naturally-occurring antibodies to specific parasite proteins.

The present invention involves synthetic peptide-based enzyme immunoassays (peptide-ELISAs) for the early detection and quantification of *P. falciparum* asexual blood-stage antibodies in sera of infected individuals from Bolivar State, Venezuela. The majority of subjects were migrant workers and their families, employed in the gold mines of Bolivar State. The nomadic activities of such individuals have made the application of malaria control programs difficult, especially in jungle regions. Malariometric indicators have Shown a progressive increase in malaria cases in Bolivar State since 1983. The annual parasite incidence (API) has steadily increased from 4.7 in 1984 to 27.4 in 1989 (Ministry of Health and Social Assistance, Venezuela). Until quite recently, P. falciparum was responsible for the majority of malaria cases in Bolivar, causing 84% of cases in 1984. Since then the situation has steadily shifted; of a total of 26,418 malaria cases in Bolivar in 1989, 61.7% were due to P. vivax and 38.3% to P. falciparum. Malaria transmission in Bolivar State is typically unstable.

In the present invention four peptides (termed C2, C3, C5, C10) were employed which were synthesized from internal chymotryptic digests of a 70 kDa P. falciparum (Indochina I/CDC) exoantigen (Pf70) found in high concentrations circulating in serum of infected individuals and in supernatant fluids of infected in vitro cultures (M. A. James et al., manuscript submitted). The 70 kDa antigen is degraded from a 120 kDa precursor membrane protein in mature schizonts and increases in amount at the time of schizont rupture (merozoite release/reinvasion) (Shamansky et al., 1985; Braun-Breton et al., 1986). Both the peptides and the native protein are highly antigenic and are conserved among diverse geographic isolates, ranging from Central and South America to Africa and Southwest Asia (Montenegro-James et al., 1988). The present study was designed to determine the extent of antibody reactivity to the 4 synthetic Pf70-derived peptides among individuals with acute malaria.

EXAMPLE 1

Antigenic Peptides

Antigen purification

The 70 kDa exoantigen was purified from supernatant fluids of continuous in vitro P. falciparum cultures using sequential chromatographic procedures previously described (Shamansky 1986; Shamansky et al. 1985). P. falciparum parasites (Indochina I/CDC strain) were cultured in vitro using human A+ erythrocytes and 10% human A+ serum (Trager and Jensen 1976). Supernatants were collected daily from asynchronous cultures at an average parasitemia of 2–3%. Supernatants were stored at –70° C. before use in purification procedures.

Exoantigens were partially purified from crude culture supernatants by SULFOPROPYL (SP)-TRISACRYL (crosslinked agarose with a propysulfonate) (Pharmacia LKB Biotechnology, Inc., Piscataway, N.J.) cation-exchange chromatography (Thelu et al. 1985). Briefly, supernatant fluids were thawed and pooled, concentrated 10 times by pervaporation at 4° C., and then dialyzed against 60 volumes of 0.01M sodium acetate buffer (pH 3.7) for 48 h at 4° C. Subsequently, this material was placed on an SP-TRISACRYL column (50×200 mm), and proteins were eluted in 0.01M sodium acetate buffer (pH 3.7) with an increasing stepwise salt gradient to 0.3M NaCl at a flow rate of 300 ml/h. Antigenic fractions (250 ml per fraction) were monitored by an enzyme-linked immunosorbent assay (ELISA) using an immune human reference serum pool [African origin; indirect fluorescent antibody (IFA) titer= 1:5,120]. Positive fractions were pooled, concentrated by lyophilization, and dialyzed against 0.01M phosphate-buffered saline (PBS) (pH 7.2) for 48 h at 4° C. These fractions, enriched for the 70 kDa exoantigen as determined by immunoblotting, were subsequently purified by a sequential high performance liquid chromatography (HPLC) series. A 3-step HPLC scheme employing gel filtration (DUPONT ZORBAX GF-250 analytical gel filtration high performance liquid chromatography column, 9.4×250 mm), diethylaminoethyl (DEAE) anion-exchange (WATERS PROTEIN PAK DEAE-5 PW, 7.5×75 mm), and phenyl hydrophobic interaction (Beckman TSK-phenyl-5PW, 7.5×75 mm) columns was used. Chromatographic conditions were carried out according to previously described procedures (Shamansky 1986; Shamansky et al. 1985). Fractions were monitored by ELISA and immunoblots. Fractions containing the 70 kDa protein were pooled, concentrated by vacuum dialysis, and then stored at –2° C. for further purification. With the use of the multi-step purification scheme (conventional cation-exchange chromatography plus sequential HPLC), the 70 kDa P. falciparum exoantigen could be routinely purified to homogeneity (confirmed by two-dimensional electrophoresis).

Enzymatic digestion and gas-phase sequencing of proteolytic fragments, analysis and synthesis of peptides Our strategy for the determination of amino acid sequences in the 70 kDa protein was to carry out a complete enzymatic digestion using chymotrypsin, followed by isolation of the resulting peptides with reverse-phase HPLC. Alpha-chymotrypsin (Sigma Chemical, St. Louis, Mo.) was used at an enzyme to protein (w/w) ratio of 1:25 to digest 500 pmoles (approximately 35 µg/ml) of the purified antigen according to the method of Stone et al. (1990b). Individual peptides were isolated by analytical reverse-phase HPLC (DELTA PAK C-18 analytical reverse-phase high performance liquid chromatography column, 3.9 mm×15 cm) according to procedures described previously (Stone et al. 1990a). Ten peptide fragments were submitted to the Genetic Engineering Facility at the University of Illinois (Urbana-Champaign, Ill.) for gas-phase sequencing. Peptides were sequenced by automated Edman degradation on an Applied Biosystems Model 470A Protein Sequencer.

All sequences were analyzed for similarities to known protein sequences, both non-malarial and malarial in origin, using the Swiss Protein Database Version 2.0 and the Malaria Protein Sequence Database (Walter and Eliza Hall Institute of Medical Research, Melbourne, Australia), respectively. No significant homologies to published sequences were found. Next, sequences were analyzed by the IBM DNASTAR software package that provided structural predictions based on computer algorithms. These included the Hopp and Woods (1981) and Kyte and Doolittle (1982) algorithms for prediction of B-cell antigenic sites (based on hydrophilicity), and the Chou and Fasman (1974) prediction of protein conformation (associated with the α-helical propensity of T-cell epitopes). With this information and other considerations four peptides (termed C2, C3, C5, C10) were selected for synthesis based on the following criteria: (i) peptide length, (ii) hydrophilicity, (iii) secondary structure, i.e., α-helices, (iv) content of proline residues. The respective peptide sequences are detailed in Table 1.

TABLE 1

Synthetic Peptides[1] Constructed from Internal Chymotryptic Digests of 70 kDa P. falciparum (Indochina I/CDC) Protein

| Peptide Fragment | Sequence[2] (No. of AA) | Secondary Structure (%)[3] | | |
|---|---|---|---|---|
| | | α-helices | β-extended | β-turn |
| 1. C2 | GQDEGEENEG SEQ ID NO: 1 (10) | 60 | 30 | 70 |
| 2. C10 | GRNGLGANTDQ-DDQLEDE SEQ ID NO: 2 (18) | 33 | 28 | 72 |
| 3. C5 | DQFFDANPNLF- | 64 | 64 | 41 |

TABLE 1-continued

Synthetic Peptides[1] Constructed from Internal Chymotryptic
Digests of 70 kDa P. falciparum (Indochina I/CDC) Protein

| Peptide Fragment | Sequence[2] (No. of AA) | Secondary Structure (%)[3] | | |
|---|---|---|---|---|
| | | α-helices | β-extended | β-turn |
| 4. C3 | QLLEPVEFDED SEQ ID NO: 3 (22) LVFLVQQPFLF- VLWDQNEKF- PVFMGVYDP SEQ ID NO: 4 (29) | 31 | 69 | 21 |

[1]Peptides ranked according to hydrophilicity.
[2]Single-letter code for amino-acid residues.
[3]Secondary structure (% amino acids) as predicted by Chou-Fasman algorithm in DNASTAR program.

Peptides C2, C3, C5 and C10 of the 70 kDa P. falciparum antigen were synthesized by the Merrifield (1963) method in an Applied Biosystems peptide synthesizer at the Genetic Engineering Facility of the University of Illinois. Peptides were lyophilized and stored in a dessicator at −20° C. until used.

The individual peptides were finally tested by ELISA for reactivity with anti-P. falciparum antibodies in sera previously collected from patients (n=126) with acute malaria from Bolivar State, Venezuela (C. S. Toebe et al., in press). Overall seropositivity (IgG) rates for peptides C2, C3, C5 and C10 were 20%, 40%, 20% and 58%, respectively. IgM reactivity to the respective peptides was 53%, 30%, 83% and 70%. It was found that immune sera from Ugandan subjects had high reactivity with the peptides (IgG seropositivity rates of 90% for C2, C3, C5 and 70% for C10). In order to improve on antigenicity and to overcome the restricted (variable) immune responsiveness to individual epitopes, the construction of a synthetic peptide hybrid was accomplished.

Preparation of a synthetic peptide complex and immunization of rabbits

Novel approach was used for the formulation of the synthetic peptide immunogen-the copolymerization of multiple peptides in the absence of carrier molecules. This results in a product unmodified by carrier conjugation and the potential effects of epitopic suppression (Leclerc et al. 1987). Peptides C2, C3, C5 and C10 were copolymerized as follows. Equal molar amounts of each peptide were mixed in PBS (pH 7.4) to affect a final protein concentration of 3 mg/ml. Peptides were polymerized with 0.6% (v/v) glutaraldehyde (final concentration), added dropwise while stirring at 25° C. Three successive additions of 0.2% glutaraldehyde were carried out, the first 2 steps were each for 10 min. and the final reaction step was for 30 min. Finally, a sodium borohydride reduction step (10 mg/ml peptide solution) was carried out for 1 h at 4° C. to reduce Schiff bases and restore the charge to the derivatized amino groups, in effect increasing the solubility of the peptide complex (Briand et al. 1985). Following copolymerization, the peptide solution was dialyzed against PBS for 48 h at 4° C. to remove free peptides and glutaraldehyde.

Three rabbits were given a series of 3 subcutaneous immunizations with the synthetic peptide complex SPf70. Peptide doses (2.5 mg) were administered at 4-week intervals. The first 2 injections were given with Freund's complete adjuvant, while the third immunization was given with Freund's incomplete adjuvant. Rabbits were bled 7 and 14 days after each immunization and the sera processed for analysis.

ELISA

The immunogenicity and antigenicity of the synthetic peptide complex was analyzed in standard microplate ELISAs. First, sera collected 14 days after the third immunization was pooled, serially diluted in PBS/0.05% TWEEN 20 (polyoxyethylene sorbitan monolaurate non-ionic detergent) from 1:50 to 1:6400, and reacted with the individual peptides and the peptide complex in a microplate ELISA. NUNC MAXICORP (Denmark) polystyrene 96-well plates were coated with either individual peptide-bovine serum albumin (BSA) conjugates, the peptide copolymer (without BSA) or BSA alone at a protein concentration of 10 μg/ml PBS pH 7.4. After a blocking/wash step with PBS/0.5% TWEEN 20, the sera were allowed to react for 2 h at 37° C. The plates were then washed three times with PBS/0.1% TWEEN 20, and then incubated with alkaline phosphatase (AP)-conjugated goat anti-rabbit IgG (H & L chains) (Kirkegaard & Perry Laboratories, Gathersburg, Md.) for 1 h at 37° C. After a final series of washes, anti-peptide IgG reactivity (absorbance values read at 405 nm and corrected for BSA control) was determined in an automated ELISA reader after a 30-min reaction period with p-nitrophenyl phosphate substrate.

In another experiment, the serum pool was diluted 1:50 and pre-incubated with the respective peptides and peptide complex at a final peptide concentration of 250 μg/ml, 25 μg/ml, 2.5 μg/ml, and no peptide. The final serum dilution was 1:100. Serum/peptides were incubated for 16 h at 4° C., and immunoprecipitates removed by centrifuging at 13,000 rpm (microcentrifuge) for 20 min. Supernatants containing antibodies were reacted in a standard peptide-ELISA with microplates coated with the homologous peptides (10 μg/ml). Antigenic reactivity was measured as described above. Finally, in a similar competitive inhibition ELISA experiment, the antigenicity of the peptides was determined after pre-incubation with hyperimmune human serum pools containing anti-P. falciparum antibodies from malaria-endemic Uganda and Venezuela (respective IFA titers=1:10, 240) and with a normal human serum control. These sera were kindly provided by Dr. I. Kakoma, University of Illinois, and Dr. O. Noya, Central University of Venezuela, respectively. The final serum dilution was 1:100. Antigenic reactivity was measured after incubation with AP-conjugated goat anti-human IgG (H & L chains) (Kirkegaard and Perry) and p-NPP substrate as described above.

Biosynthetic labelling/immunoprecipitation, and immunoblotting of P. falciparum antigens.

In vitro cultures of the Geneve/SGE-1 strain of P. falciparum were synchronized by sorbitol lysis, and late-stage parasitized erythrocytes were concentrated using PERCOLL (colloidal polyvinylpyrridolone coated silica for cell separation). Stage-specific labelling of schizont proteins (approx. 70% parasitemia) was carried out using $^{35}$S-methionine in RPMI 1640 plus 10% human serum (1mCi/5 ml) for 5 h according to standard procedures. Schizonts were removed by centrifugation, lysed in cold 10 mM Tris buffer (pH 8) and solubilized in 1% NONIDET P-40 (octylphenol-ethylene oxide condensate) in PBS. IgG fractions (rabbit anti-peptide complex and normal rabbit control) were coupled to Protein-A-SEPHAROSE CL-4B (beaded crosslinked agarose), washed and subsequently incubated with 200 μl of labelled parasite extract. After a final washing, 100 μl of sodium dodecyl sulfate (SDS)/dithiothreitol (DTT) sample buffer was added to each immunoprecipitate (IP), boiled for i min and centrifuged. Sixty μl of each IP supernatant was loaded onto a 10% SDS-PAGE gel and electrophoresed at 70 V for 20–24 h. The gels were enhanced for fluorography, and films developed by standard procedures.

*Plasmodium falciparum* (Indochina I/CDC strain) antigens (infected erythrocyte lysate and affinity-purified exoantigens) from asynchronous in vitro cultures were analyzed by SDS-PAGE followed by immunoblotting. Exoantigens were affinity-purified from culture supernatant fluids using monoclonal anti-peptide C3 and human anti-*P. falciparum* antibodies (generously provided by Dr. I. Kakoma) on REACTI-GEL coloumns (activated solid support cross linked 1 1' carbonylidiimidazole) (Pierce Chemical, Rockford, Ill). Electrophoresis was performed on 10% acrylamide gels under non-reducing conditions. After transfer, antigens were reacted with 1:100 dilutions of sequentially collected rabbit antisera (day 0, days 7 and 14 post-first immunization, day 7 post-second immunization) to the SPf70 copolymer. The antigens were subsequently developed after incubation with horseradish peroxidase (HRPO)-conjugated goat anti-rabbit immunoglobulins (Kirkegaard & Perry) and diamine benzidine substrate.

Results

Figure 1B:
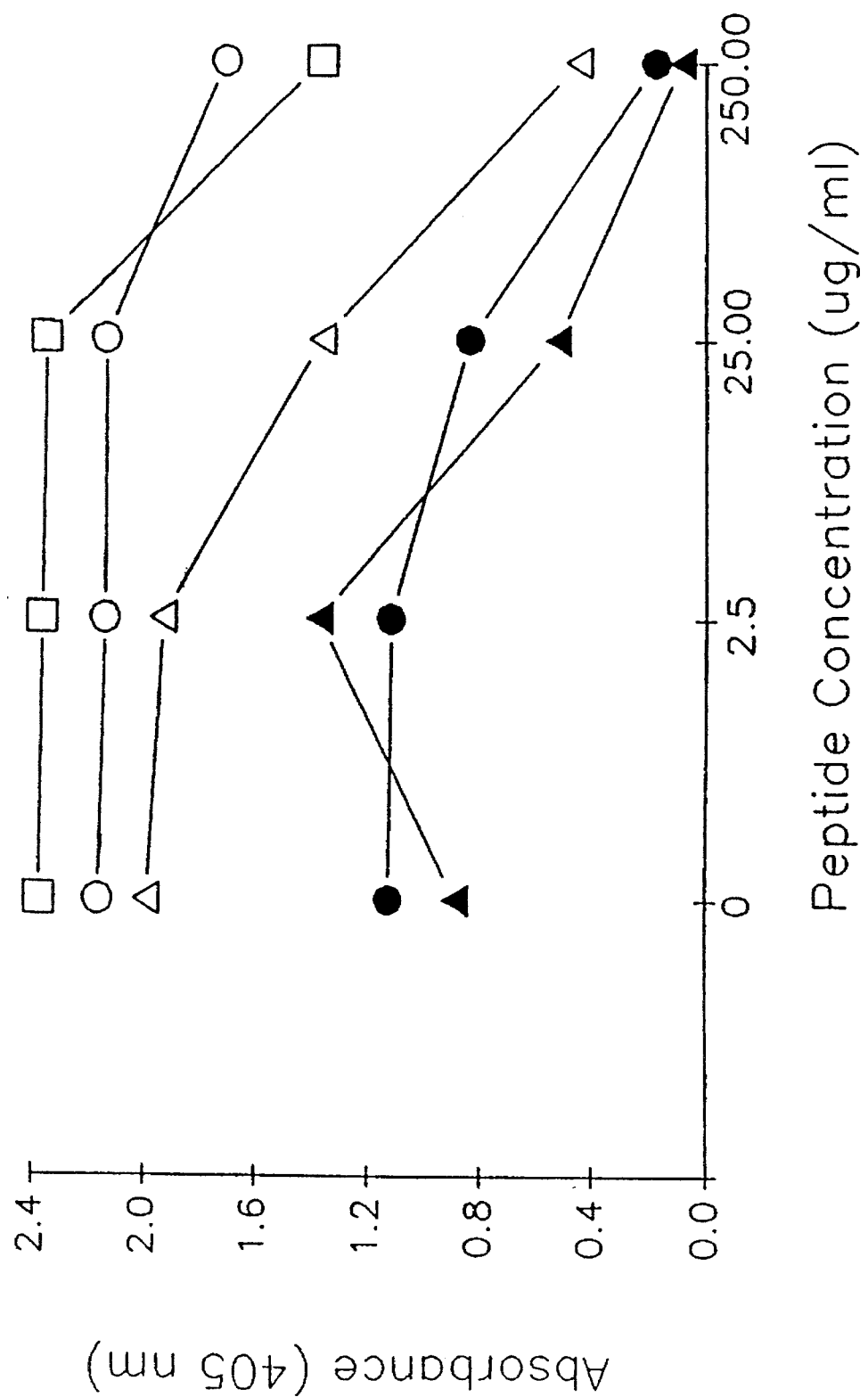

The present study showed that a unique set of peptides (termed C2, C3, C5 and C10), derived from a 70 kDa *P. falciparum* exoantigen, could be effectively used as a synthetic immunogen (SPf70) when copolymerized with glutaraldehyde in the absence of a carrier. The synthetic peptide complex when administered with Freund's adjuvant was found to be highly immunogenic in rabbits. Specific anti-peptide responses were analyzed by conventional peptide-ELISA (FIG. 1A and 1B). Serologic reactivity to the peptide complex and peptides C2 and C5 was uniformly high, followed by the responses to C3 and C10. Normal rabbit serum gave negligible background reactivity (data not shown). These data suggest that the most immunogenic epitopes are components of peptides C2 and C5. The efficacy of C2 and C5 for eliciting high levels of T-dependent antibody (IgG) may be correlated with the presence of putative T-cell epitopes as demonstrated by their respective content of alpha-helices (Table 1). Moreover, antibodies to the peptide complex are reactive with *P. falciparum* schizonts as demonstrated by indirect immunofluorescence assays, with titers ranging from 1:320–1:640 after the third immunization.

Figure 2A:
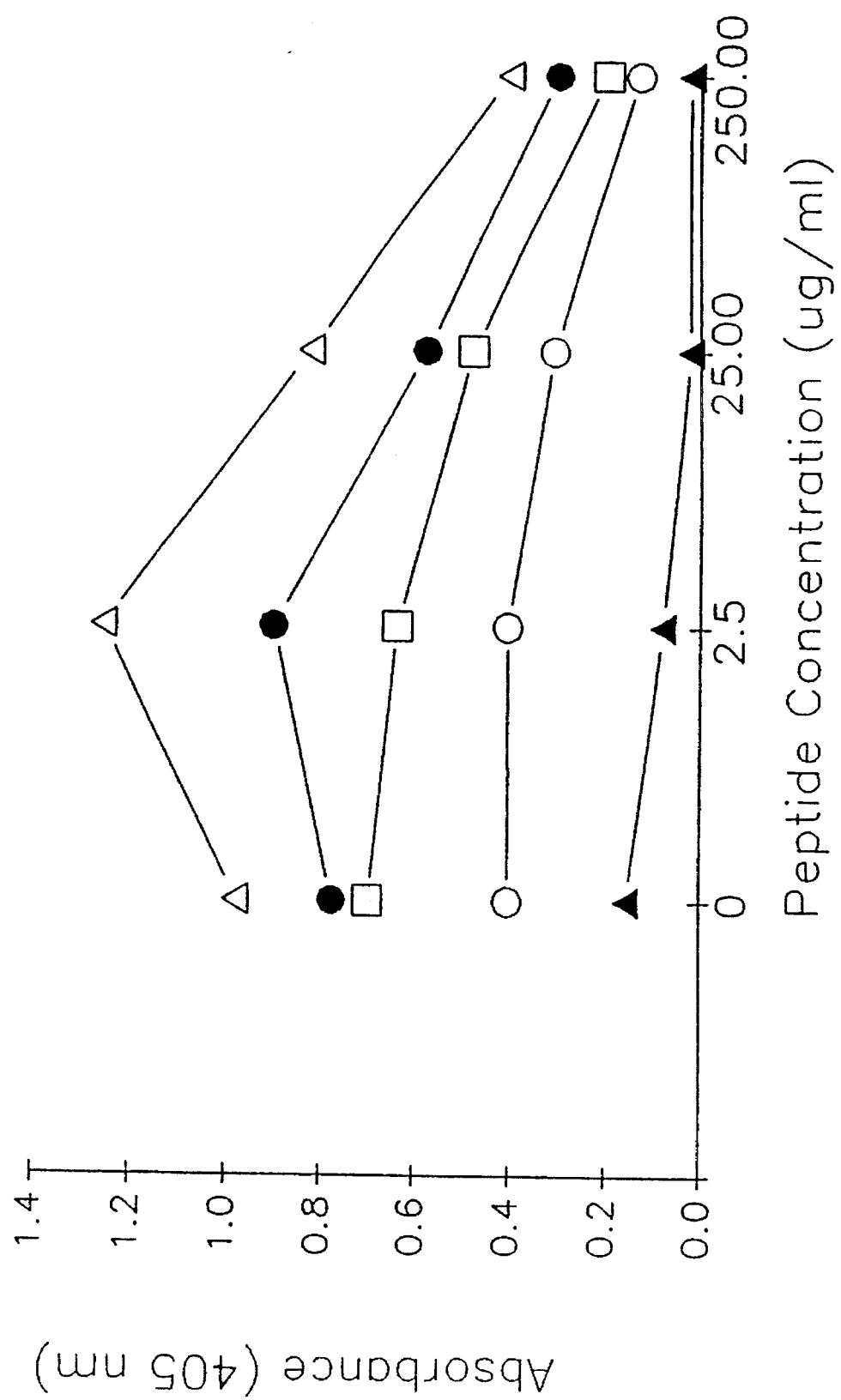
FIGS. 2A and 2B. concern the antigenicity of synthetic peptides derived from the 70 kDa *P. falciparum* exoantigen. Hyperimmune human serum pools containing anti-*P. falciparum* antibodies from malaria-endemic Uganda (FIG. 2A) and Venezuela (FIG. 2B) were pre-incubated with peptides C2, C3, C5, C10 and the peptide complex (PC) prior to measuring antigenic reactivity of homologous peptides in a standard peptide-ELISA.
Figure 2B:
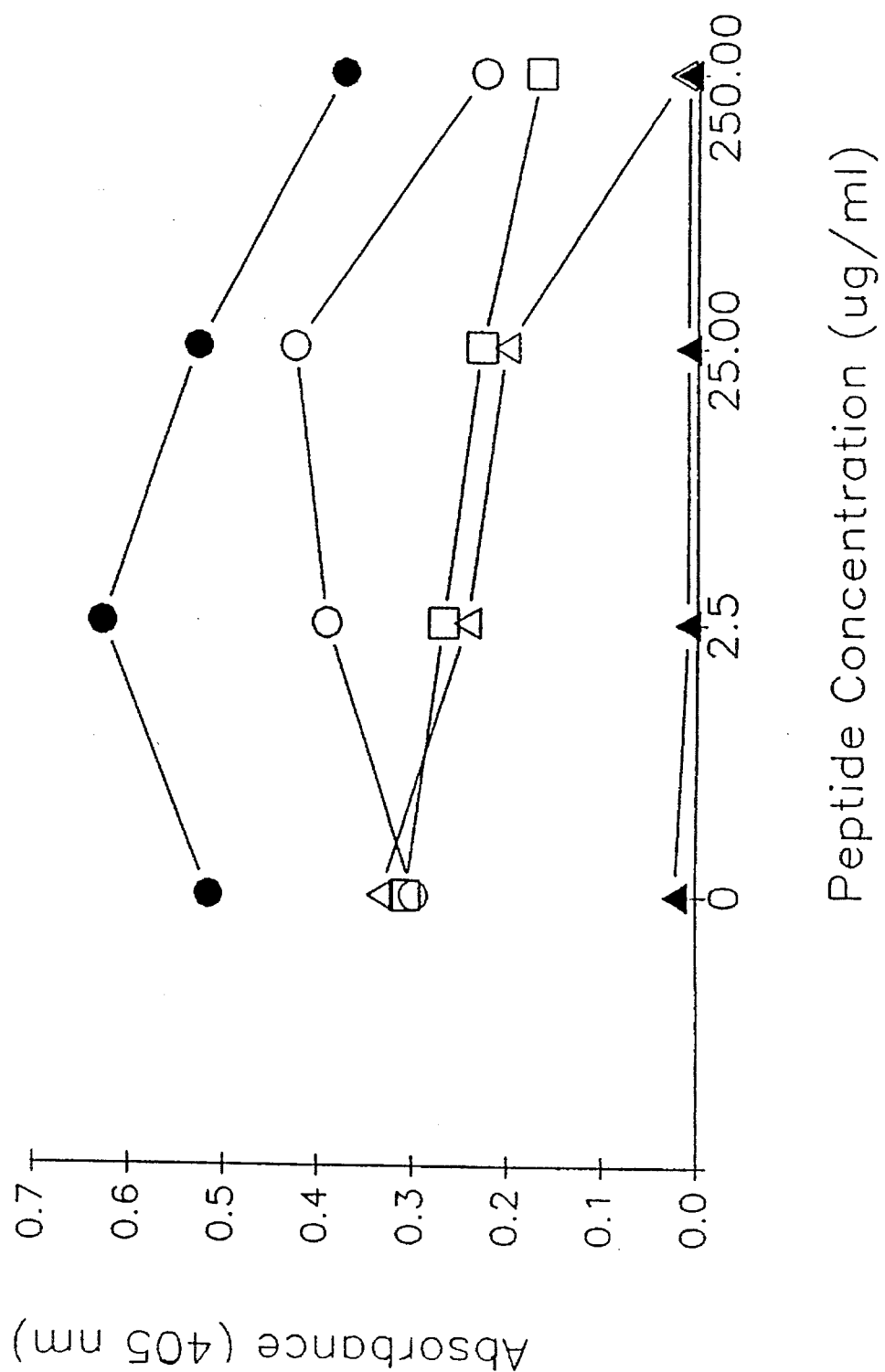
Figure 3:
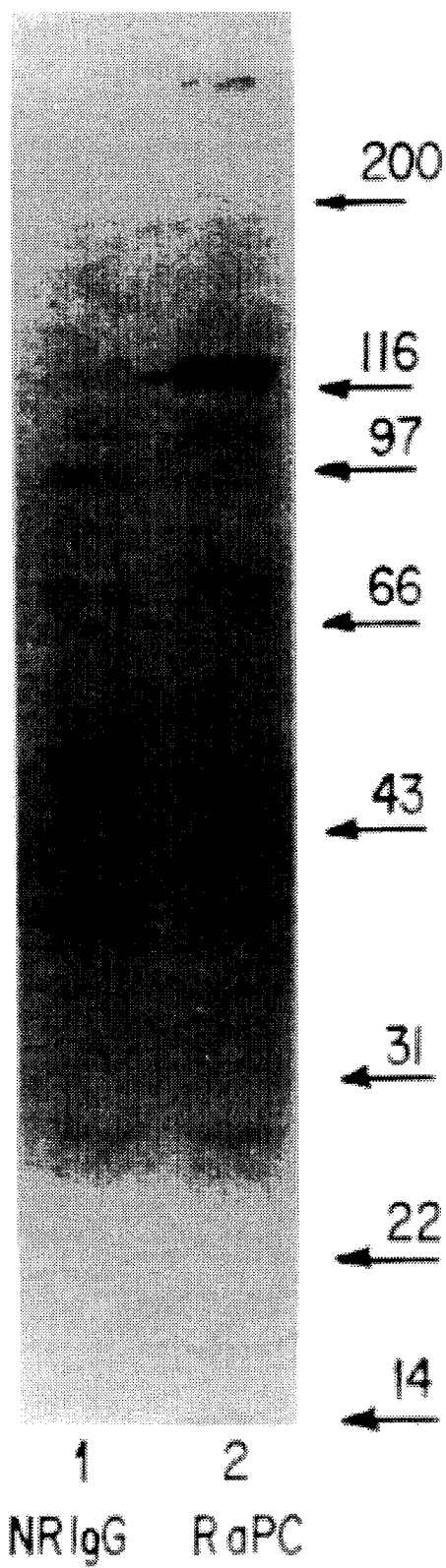
FIG. 3 relates to the biosynthetic labelling and immunoprecipitation of *P. falciparum* antigen. $^{35}$S-methionine labelled-*P. falciparum* (Pf) Geneve/SGE-1 schizonts were solubilized and immunoprecipitated with rabbit anti-peptide complex (R aPC) IgG (lane 2). Normal rabbit IgG (NR IgG) was used as a control (lane 1). A major 120 kDa *P. falciparum* antigen precipitated by immune IgG is indicated with an arrow.
Figure 4:
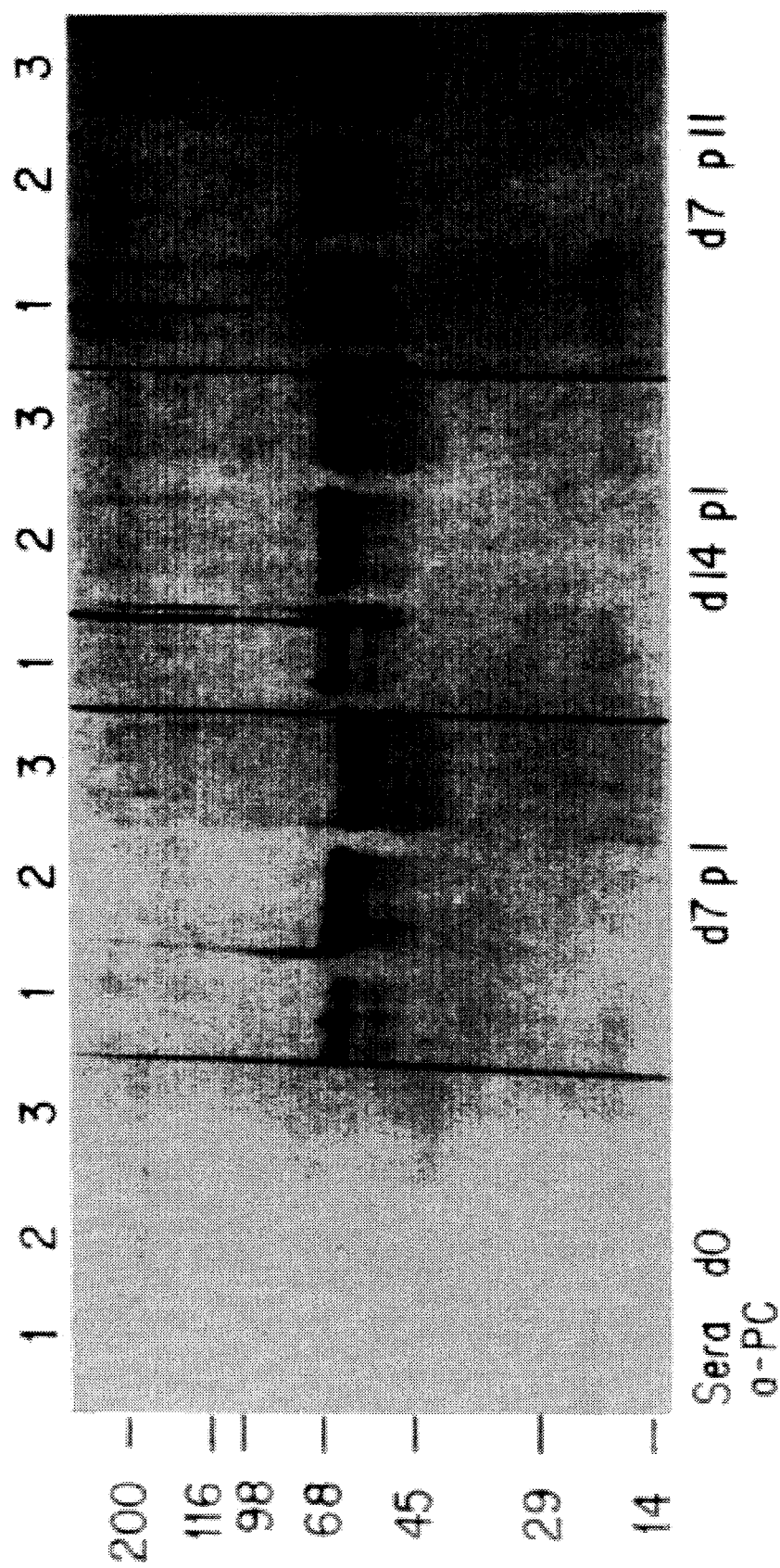
FIG. 4 concerns SDS-PAGE/immunoblotting of the 70 kDa *P. falciparum* protein. Antigens from *P. falciparum* Indochina I/CDC in vitro cultures (infected erythrocyte lysate, lane 1; exoantigen affinity-purified with monoclonal antibody to peptide C3, lane 2; exoantigens affinity-purified with immune IgG from Ugandan subjects, lane 3) were reacted in immunoblots with antisera (pooled) collected sequentially from rabbits immunized with the SPf synthetic peptide complex (PC). Sera collected 7 and 14 days (d7, d14) after the first (PI), and second (d7 pII), immunizations were compared with baseline (d0) sera.

Peptide antigenicity was assessed with human anti-*P. falciparum* sera from malaria-endemic regions of Uganda and Venezuela. ELISA data showed that anti-*P. falciparum* antibodies were specific for and reactive with the peptides (FIG. 2A and 2B). With the exception of peptide C10, all peptides demonstrated good antigenic reactivity (particularly C3). Normal human serum gave minimal background reactivity (mean absorbance value=0.11). Greatest reactivity was seen with the Ugandan sera. The lesser reactivity with antibodies in Venezuelan immune sera may be because of strain differences or may indicate a lower level of naturally-acquired anti-70 kDa (and anti-peptide) antibodies in the sera. The specificity of the rabbit anti-SPf70 antibodies for *P. falciparum* antigen was shown by immunoprecipitation of metabolically labelled proteins (FIG. 3) and by immunoblotting (FIG. 4). The major protein precipitated by anti-peptide complex (PC) IgG was a 120 kDa schizont antigen. Several other minor proteins were also precipitated nonspecifically by normal rabbit IgG. It appears that the 120 kDa membrane protein is degraded in mature schizonts to the 70 kDa exoantigen which increases in amount at the time of merozoite release/reinvasion (Braun-Breton et al. 1986). At this point, a substantial amount of 70 kDa antigen is released into the surrounding medium. Hyperimmune sera collected sequentially from rabbits immunized with the synthetic copolymer reacted in immunoblots (FIG. 4) with the 70 kDa antigen from (1) *P. falciparum* Indochina I-infected erythrocyte extracts, (2) supernatant fluid, i.e., exoantigens, from Indochina I cultures affinity-purified with monoclonal antibody to peptide C3, (3) Indochina I exoantigens affinity-purified with *P. falciparum*-immune IgG of Ugandan origin.

Discussion

Described herein are peptide sequences of a 70 kDa *P. falciparum* exoantigen (Pf70), that when synthesized and constructed as a copolymer (SPf70), are able to induce the formation of antibodies that are reactive with the native malarial protein. The knowledge of peptide sequences allowed the construction of synthetic peptides representing immunodominant, and immunorelevant, epitopes of the native protein. If Pf70 is involved in the induction of TNF production in clinical malaria, the present approach is to design and construct a synthetic immunogen that improves upon nature. With the careful selection of parasite-specific epitopes, the present invention enhances immunogenicity and induces a solid immunity against disease (Berzofsky 1991; Good and Miller 1990).

In this phase of studies, the construction of the synthetic peptide hybrid was carried out by glutaraldehyde copolymerization (Leclerc et al. 1987). Although glutaraldehyde copolymerization results in a relatively random-linked product, this randomized relationship of multiple parasite-specific B-cell and T-cell epitopes meets the requirements for induction of potent immune (antibody- and T cell-mediated) responses. The high antigenic reactivity of SPf70 and the individual component peptides demonstrated the induction of T cell-dependent antimalarial antibody (IgG) responses, and is consistent with the use of such synthetic peptide polymers as immunogens and diagnostic reagents (together with anti-peptide antibodies for the detection of antigen). Of course, numerous other cross-linking agents are known and should be usable in place of glutaraldehyde.

One of the important indicators of functional immunity to malaria is the recognition of malarial antigens or synthetic derivatives by defined sera from human populations immunized by natural exposure to *P. falciparum*. Recent studies with epidemiologically-defined populations from Indonesia, Brazil and Africa (Burkina Faso) have shown anti-SPf70 reactivity to correlate with naturally-acquired protective-immunity. The first study was conducted by J. K. Baird et al. (unpublished data). A total of 218 serum samples from Irian Jaya were analyzed for antibody to SPf70 by ELISA. Sera were collected from individuals during a malaria epidemiologic study by Baird et al. (1991). Subjects were grouped according to age and immune status (recent vs. lifelong residents). Antibody reactivity to SPf70 was found to increase with age among migrant people with only 2 years exposure to hyperendemic malaria. The increased frequency and level of anti-SPf70 antibody among 110 migrants was quantitatively parallel to that among 100 lifelong residents of the hyperendemic area. Overall, 83% of the people had antibodies reactive with SPf70. The proportion of people positive for anti-SPf70 antibody increased from 45% among 2 to 5-year olds, to 95 to 100% among adults (>15 years of age).

The second study was conducted by C. D. Ribeiro et al. In a seroepidemiologic study designed to assess the natural humoral response to various *P. falciparum* antigens including Pf70, the humoral immune recognition of SPf70 was analyzed by ELISA. Sera were collected from diverse human populations, e.g., Amazonian Indians and hyperimmune Africans from Burkina Faso. Seropositivity rates for antibodies reactive with SPf70 were 58% for the Amazonian subjects and 85% for the population from Burkina Faso.

This compared with rates of 51% and 20%, respectively, for antibodies to a NANP$_4$ peptide derived from the central repeat region of the circumsporozoite protein. The present inventors provided SPf samples for that study, although its structure was withheld.

The above studies indicate that the target Pf70 peptides are immunogenic in nature (no obvious genetic restriction) as 85% of hyperimmune West African adults and 95–100% of immune Irian Jayan adults possess antibodies to Pf70. Moreover, the present results confirm the immunogenicity and antigenic reactivity of the synthetic peptide complex SPf70.

EXAMPLE 2

DETECTION OF ANTIBODIES TO A 70 kDa PLASMODIUM FALCIPARUM EXOANTIGEN IN MALARIOUS SUBJECTS USING SYNTHETIC PEPTIDES OF THE PRESENT INVENTION

Materials and Methods
Subjects

Serum samples (n=126) were collected between 1985–1989 from patients diagnosed with acute malaria attending the malaria outpatient clinics of the Malariology Service of the Ministry of Health and the Hospital Ruiz y Paez in Ciudad Bolivar, Bolivar State, Venezuela. Diagnosis was made on the basis of clinical symptoms and the detection of parasites in Giemsa-stained blood films. Of the 126 patients, 34 were documented as experiencing a primary malaria episode and 58 as having more than one episode. In addition, of the patients for whom definitive diagnosis of the infecting species was known, 57 were positive for *P. falciparum* and 28 for *P. vivax*. Serum samples were also collected from 20 individuals with no history of malaria at Charity Hospital, New Orleans, La., USA. All sera were stored at −70° C. prior to analysis.
Indirect immunofluorescent antibody assays For the indirect immunofluorescent antibody (IFA) assays, thin smears of *P. falciparum* (Indochina I/CDC strain)-infected monkey erythrocytes were prepared as antigen slides and fixed in acetone for 15 min. Serum samples were diluted in phosphate-buffered saline (PBS) (initial dilutions 1:20 and 1:40) and allowed to react with antigen for 30 min at 37° C. The slides were then washed twice in PBS and once in distilled H$_2$O (5 min each). Commercial fluorescein-conjugated anti-human IgM and IgG (Cappel Laboratories, Malvern, Pa., U.S.A.) were used as second antibodies diluted 1:40 in PBS. Two-fold dilutions of test sera were also titered for IgG and IgM antibodies (initial dilution 1:80) using heavy chain-specific fluorescein-conjugated anti-human IgG and IgM (Cappel Laboratories) for determination of total anti-asexual blood-stage antibody levels.
Enzyme-linked immunosorbent assay An enzyme-linked immunosorbent assay (peptide-ELISA) adapted from the method of Deloron et al., (1989) was used to determine antibody reactivity to synthetic peptides. Peptides were conjugated to bovine serum albumin (BSA) at a molar ratio of 25:1 (peptide to BSA) with glutaraldehyde in PBS. After passage over a G-25 SEPHADEX column (dextran cross linked with epichlorohydrin), peptides were stored frozen and used at a final concentration of 5 μg/ml. As control antigens, BSA-glutaraldehyde was prepared at 2.5 μg/ml and *P. falciparum* (Venezuelan strain)-infected erythrocyte lysate at 200 μg/ml. Flat-bottom, 96-well IMMULON II, polystyrene (Dynatech Laboratories, Alexandria, Va., U.S.A.) plates were coated with antigens for 2 h at 37° C., blocked/washed twice for 10 min each in PBS containing 0.5% Tween-20 (PBS-T) and rinsed with distilled H$_2$O. Sera were diluted 1:100 in PBS-T containing 5% non-fat dry milk and 0.3% BSA-glutaraldehyde (BLOTTO-G) and applied to duplicate wells for 2 h at 37° C. and then washed in PBS-T as before. Alkaline phosphatase-conjugated anti-human IgG or IgM were added at a 1:750 dilution in BLOTTO-G and incubated for 1 h at 37° C. After a final wash, 100 μl of p-nitrophenol phosphate substrate was added and allowed to react for 1 h at room temperature. Absorbance values were measured by reading the optical density (OD) at a wavelength of 405 nm. Test sera were considered antibody-positive when the absorbance value was greater than the mean OD+2 standard deviations obtained with control sera.
Results All of the patients (n=126) diagnosed with acute malaria were positive at screening dilutions of 1:20 and 1:40 for anti-*P. falciparum* asexual blood-stage IgG antibodies as determined by the IFA. Of these, 105 (83%) were also positive for anti-malarial IgM antibodies. All positive sera were subsequently titrated using two-fold dilutions (initial dilution 1:80) for IgG and IgM antibodies, respectively. There was a trend toward higher IgG titers with increasing age (not shown) but correlations between antibody levels and age were complicated as subjects less than 20 years old attending the clinic were under-represented. Patients known to have experienced more than one malarial episode (n=58) had significantly higher mean IgG levels (p<0.05) than those with primary malaria infections (n=34) (Table 2).

TABLE 2

| Antibody responses and exposure to malaria | | | |
|---|---|---|---|
| | | Geometric mean IFA titer[a] (standard deviation) | |
| Exposure | n = 92 | IgG | IgM |
| Primary | 34 | 7.76 (2.72) | 6.90 (2.55) |
| Repeated[b] | 58 | 8.96 (2.51) | 6.61 (2.92) |

[a]The geometric mean IFA titer of IgG antibodies to *P. falciparum* (Indochina I/CDC strain) asexual blood-stage antigens increased significantly with more than one malarial episode (b) (P = 0.035, by ANOVA). Although IgM levels were higher in individuals experiencing their first malarial episode, the difference was not statistically significant.

Figure 5:
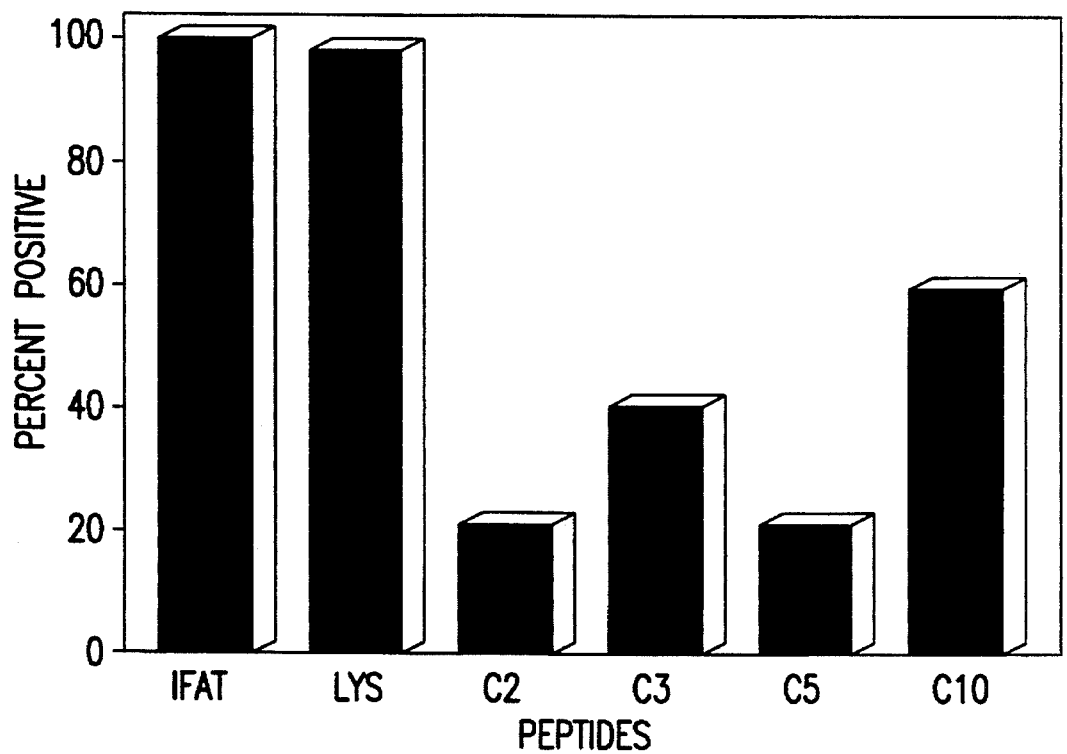
FIG. 5 shows the percentage of sera positive for anti-*P. falciparum* IgG antibodies by IFA and peptide-ELISA (n=126).IFA=indirect fluorescent antibody test; LYS=*P. falciparum*-infected erythrocyte lysate preparation (see methods).
Figure 6:
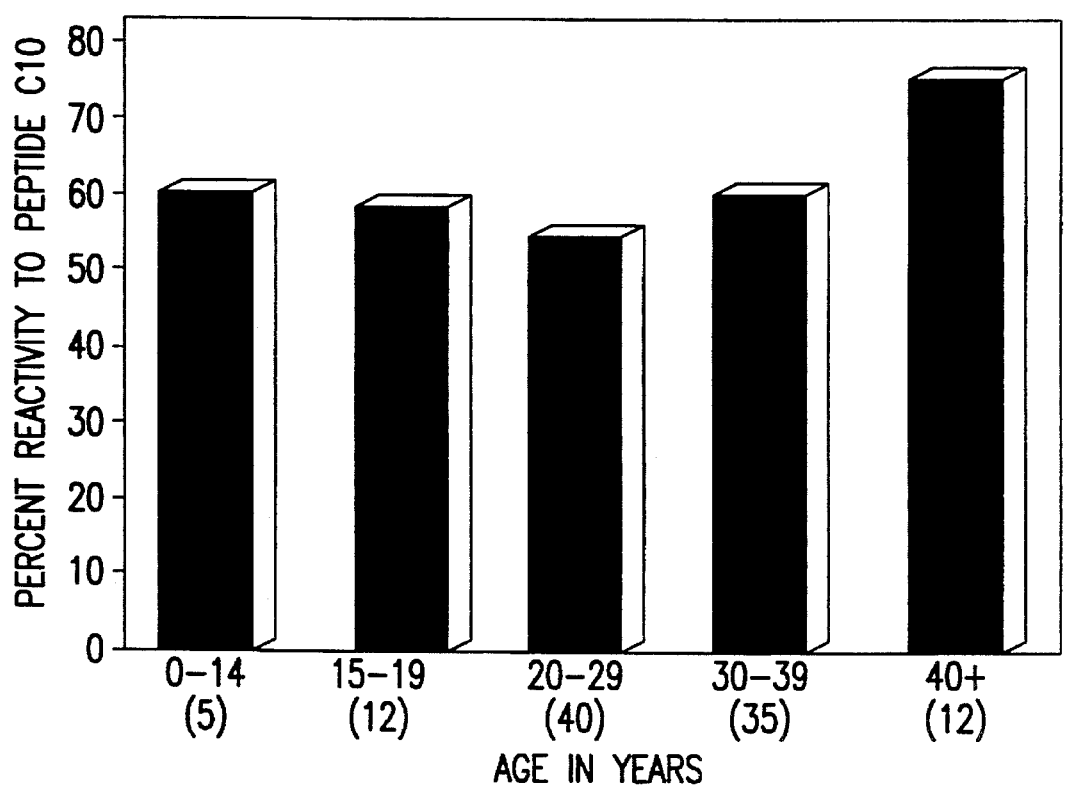
FIG. 6 shows the age distribution of anti-*P. falciparum* IgG reactivity to synthetic peptide C10 (n=104). Numbers in parentheses indicate number of patients in each age group.

The respective cut-off values (mean OD level+2 standard deviations) of the 20 control sera used in peptide-ELISAs was 0,065 for C2, 0.066 for C3, 0.009 for C5, 0.020 for C10 and 0.486 for the *P. falciparum* lysate antigen. Of the patients with acute malaria, 123 (97.6%) reacted with the *P. falciparum* lysate, reflecting a high correlation with IFA reactivity. Each of the three patients that tested negative had low IgG titers (≦320) by IFA. Overall seropositivity rates of the subjects to the respective peptides were C2=20%, C3=40%, C5=20% and C10=58%. The results of IgG reactivity by IFA and ELISA are summarized in FIG. 5. Due to the limited number of subjects under 20 years old, a relationship between peptide reactivity and age could not be determined. However, C10 showed the greatest reactivity, ranging from 53 to 75% seropositivity among different age groups of malarious subjects (n=104) (FIG. 6).

Selected sera, categorized on the basis of primary or repeated exposure to malaria, were tested for IgM antibody reactivity in peptide-ELISAs. Preliminary results indicated that except for C3, overall IgM reactivity to each peptide was relatively high with maximal reactivity to C5 (83%).

IgM reactivity was generally greater in patients with primary malaria infections. This pattern was more distinct among sera with higher IgM titers and for sera reacting to C5 and C10 (Table 3).

TABLE 3

Percentage of sera positive by peptide-ELISA for IgM (μ chain-specific) antibody

| IgM Titer[a] | Exposure | PEPTIDES (PERCENT POSITIVE) | | | |
|---|---|---|---|---|---|
| | | C2 | C3 | C5 | C10 |
| HIGH | P | 80 | 20 | 80 | 100 |
| | R | 40 | 0 | 60 | 60 |
| MEDIUM | P | 80 | 20 | 100 | 100 |
| | R | 40 | 80 | 80 | 60 |
| LOW | P | 20 | 20 | 80 | 40 |
| | R | 60 | 40 | 80 | 40 |
| TOTAL REACTIVITY: (n = 30) | | 53.3 | 30 | 83.3 | 70 |

[a]Reciprocal IgM titers determined by IFA (range: Low = 40–1,280, Medium = 2,560–5,120, High = 10,240–40,960). P = Primary malarial infection. R = Repeated malarial infection. Five sera were assessed in each group. Cut-off values (mean OD + 2 standard deviations of control sera) for determining positive reactions were as follows: C2 = 0.122, C3 = 0.029, C5 = 0.019, and C10 = 0.051.

Discussion

The present study was designed to characterize the antibody responses of subjects with acute malaria from Bolivar State, Venezuela to synthetic peptides derived from a 70 kDa *P. falciparum* (Indochina I/CDC strain) exoantigen. All patients had asexual blood-stage antibodies to the Indochina I strain as determined by IFA. IgG titers were correlated with exposure to malaria. A large proportion (83%) of subjects also possessed IgM antibodies as determined by IFA, indicative of the early course of infection. The overall level of IgG reactivity to synthetic peptides derived from Pf70 was C2=20%, C3=40%, C5=20% and C10=58%. Seropositivity to peptide C10 was consistently over 50% (range 53–75%) among patients of different age groups.

In the present study, preliminary investigations with selected sera from patients with anti-malarial IgM antibodies indicated that, with the exception of C3, the level of reactivity to peptides was generally high: C2=53%, C5=83% and C10=70%. Reactivity was generally greater in individuals with a primary malaria episode. Given the fact that IgM levels wane much sooner than IgG during a malarial infection, IgM-specific reactivity may serve as a useful indicator of recent exposure to the parasite for diagnostic purposes (Shehata et al., 1988).

This and previous studies in the inventors' laboratory have demonstrated that the Pf70 peptides do not cross-react with non-malaria parasites, although they are reactive with *P. vivax* antibodies (Montenegro-James et al.). This point is advantageous from the standpoint of early diagnosis as a general 'malaria'-specific peptide would not only be useful but desirable for initial screening prior to speciation (Chiodini and Moody, 1989).

As mentioned, malaria transmission in Bolivar is unstable and the majority of individuals in this study were migrant workers and their families who were only intermittently exposed to malaria in gold-mining areas of the state. Sanchez et al. (1990) noted that in such subjects ELISA values for serological reactions to crude *P. falciparum* asexual blood-stage antigens are often low or negative. In addition, all of the subjects in this study were suffering from acute malaria. In such patients, other investigators have observed low seropositivity rates and antibody levels to various blood-stage antigens suggestive of disease-induced immunosuppression (Deloron et al., 1989; Petersen et al., 1989).

Seroepidemiologic surveys that have used other malarial antigens have shown that antibody levels fall rapidly in the absence of repeated infections (Tapchaisri et al., 1985; Mendis et al., 1992) and that antibody responses vary among people at equal risk of exposure to malaria (Rosenberg and Wirtz, 1990) which may be explained in part by genetic restriction (Chizzolini et al., 1988). The limited number of epitopes on a given peptide may also fail to be recognized by a number of subjects with intermittent experience of malaria. A study conducted by Mendis et al. (1992) in Sri Lanka, where malaria transmission is also unstable, found that antibodies to the CS protein of either *P. vivax* or *P. falciparum* were present in less than 20% in the population as a whole, despite a life-long exposure to *P. vivax*. Thus, it was concluded that in such areas, seropositivity may reflect differences in exposure to inoculation versus a cumulative experience of malaria.

One skilled in the art can see that the antibodies induced to the circulating malarial antigens of the present invention can, in turn, be purified and used as a reagent for assaying the level of circulating malarial antigens in a patient. These prepared antibodies are affixed to a surface and incubated with a biological sample from the patient to allow immunoreaction to occur. The detection of circulating malarial antigens is accomplished by contacting the immunoreacted product with an indicator antibody directed to the malarial antigens bound to the affixed antibodies.

The biological sample from the patient may be serum or plasma, in particular, human serum or plasma. The indicator antibody may be an enzyme linked antibody, a fluorescent tagged antibody or a radiolabeled antibody.

EXAMPLE 3

THE USE OF COMPOSITE IMMUNOGEN SPf70 AS A VACCINE IN HUMANS

The SPf70 protein will be reconstituted (if lyophilized) in 0.9% saline solution and adsorbed onto alum hydroxide at a concentration of 4 mg of synthetic protein and 2 mg of $Ai(OH)_3$/ml. The vaccine will be kept at 4° C. before use. A dose of 2 mg SPf70 in 0.5 ml will be injected subcutaneously for each adult individual. Children less than 5 years old will receive half this dosage. The vaccination schedule will consist of 3 doses administered on days 0, 30, and 180.

In conclusion, the synthetic peptides employed in this study, representing epitopes of a native 70 kDa *P. falciparum* exoantigen can be used for the detection of asexual blood-stage antibodies in malaria-endemic regions and in epidemiological settings which measure their relative antigenicity, specificity and conservation between *P. falciparum* strains. Further investigations described herein demonstrate the antigenic use of these peptides as a hybrid molecule (SPf70), thereby increasing the number of epitopes available for immune reactivity (see Example 1).

REFERENCES

Baird et al. (1991). Age-dependent acquired protection against *Plasmodium falciparum* in people having two years exposure to hyperendemic malaria. *Am J Trop Med Hyg* 45: 65–76.

Bate et al. (1990). Malaria exoantigens induce T-independent antibody that blocks their ability to induce TNF. *Immunology* 70: 315–320.

Berzofsky J.A. (1991). Mechanisms of T cell recognition with application to vaccine design. *Mol Immunol* 28: 217–223.

Braun-Breton, et al. In vivo time course of synthesis and processing of major schizont membrane polypeptides in *Plasmodium falciparum*. *Mol. Biochem. Parasitol.* 20 (1986) 33–43.

Briand et al. (1985). Synthetic peptides as antigens: pitfalls of conjugation methods. *J Immunol Meth* 78: 59–69.

Campbell, et al. Use of synthetic and recombinant proteins in the study of host-parasite interactions in the malarias. *Amer. J. trop. Med. Hyg.* 37 (1987) 428–444.

Chiodini, et al. Techniques for the detection of malaria parasites. *J. Roy. Soc. Med, Suppl.* 17, 82 (1989) 41–43.

Chizzolini, et al. Natural antibodies against three distinct and defined antigens of *Plasmodium falciparum* in residents of a mesoendemic area in Gabon. *Amer. J. Trop. Med. Hyg.* 39 (1988) 150–156.

Chizzolini, et al. Age-related prevalence of antibody response against three different, defined *Plasmodium falciparum* antigens in children from the Haut-Ogooue province in Gabon. *Trans. Roy. Soc. Trop. Med. Hyg.* 83 (1989) 147–151.

Chou et al. (1974). Prediction of protein conformation. *Biochemistry* 13: 222–245.

Deloron, et al. Antibodies to *Plasmodium falciparum* ring-infected surface antigen and *P. falciparum* and *P. malariae* circumsporozoite proteins: seasonal prevalence in Kenyan villages. *Amer. J. Trop. Med. Hyg.* 41 (1989) 395–399.

Deloron, et al. Antibodies to the reng-infected erythrocyte surface antigen and the circumsporozoite protein of *Plasmodium falciparum* in a rural community from Burkina Faso. *Trans. Roy. Soc. Trop. Med. Hyg.* 84 (1990) 191–195.

Esposito, et al. Prevalence and levels of antibodies to the circumsporozoite proteins of *Plasmodium falciparum* in an endemic area and their relationship to resistance against malaria infection. *Trans. Roy. Soc. Trop. Med. Hyg.* 82 (1988) 827–832.

Good et al. (1990). T-cell antigens and epitopes in malaria vaccine design. *Curr Top Microbiol Immunol* 155: 65–78.

Grau et al. (1989). Tumor necrosis factor and disease severity in children with falciparum malaria. *New Engl J Med* 320: 1586–1591.

Hopp et al. (1981). Prediction of protein antigenic determinants from amino acid sequences. *Proc Natl Acad Sci USA* 78: 3824–3828.

James et al. (1985). Induction of protective immunity to *Plasmodium falciparum* in *Saimiri sciureus* monkeys with partially purified exoantigens. *Infect Immun* 49:476–480.

Karunaweera et al. (1992). Dynamics of fever and serum levels of tumor necrosis factor are closely associated during clinical paroxysms in *Plasmodium vivax* malaria. *Proc Natl Acad Sci USA* 89: 3200–3203.

Kwiatkowski et al. (1989). Tumour necrosis factor production in *falciparum* malaria and its association with schizont rupture. *Clin Exp Immunol* 77: 361–366.

Kwiatkowski et al. (1990). TNF concentration in fatal cerebral, non-fatal cerebral, and uncomplicated *Plasmodium falciparum* malaria. *Lancet* 336: 1201–1204.

Kyte et al. (1982). A simple method for displaying the hydropathic character of a protein. *J Mol Biol* 157: 105–132.

Leclerc et al. (1987). A synthetic vaccine constructed by copolymerization of B and T cell determinants. *Eur J Immunol* 17: 269–273.

Mendis, et al. Anti-circumsporozoite protein antibodies measure age related exposure to malaria in Kataragama, Sri Lanka. *Parasite Immunol.* 14 (1992) 75–86.

Mendis K.N. (1992). Contrasting clinical disease in *Plasmodium vivax* and *Plasmodium falciparum* malaria, and the association of both with cytokines. *Bull Inst Pasteur* 90: 3–9.

Merrifield R.B. (1963). Solid phase peptide synthesis. I. The synthesis of a tetrapeptide. *J Am Chem Soc* 85: 2149–2154.

Molyneux M. (1990). Cerebral malaria in children: clinical implications of cytoadherence. *Am J Trop Med Hyg* 43, suppl.: 38–41.

Montenegro-James et al. *Abstr. Annu. Meet. Am. Soc. Trop. Med. Hyg.* 1988, 175, pg. 154.

Petersen, et al. An epidemiological study of humoral and cell-mediated immune responses to the *Plasmodium falciparum* antigen Pf155/RESA in adult Liberians. *Amer. J. Trop. Med. Hyg.* 41 (1989) 386–394.

Playfair et al. (1991). Don't kill the parasite: control the disease. *Acta Leid* 60: 157–165.

Playfair et al. (1990). The malaria vaccine: anti-parasite or anti-disease? *Immunol Today* 11: 25–27.

Ribeiro et al., (1991) *Proc. IV Intl. Cong. Malaria & Babesiosis*, Abstr. 2.22.

Rosenberg, et al. Intrinsic individual differences in circumsporozoite antibody response at a hyperendemic malaria focus. *Trans. Roy. Soc. Trop. Med. Hyg.* 84 (1990) 206–208.

Sanchez, et al. Malaria in the Amazon. Prevalence of *Plasmodium falciparum* antibodies in Amerindians inhabiting the Venezuelan Amazon. *Ann. Trop. Med. Parasit.* 84 (1990) 307–312.

Scuderi et al. (1986). Raised serum levels of TNF in parasitic infections. *Lancet ii:* 1364–1365.

Shamansky L.M. (1986). Purification and characterization of soluble antigens from the human malaria parasite *Plasmodium falciparum*. Ph.D. thesis, University of Illinois, Urbana-Champaign, Ill.

Shamansky, et al. Purification and characterization of culture-derived exoantigens of *Plasmodium falciparum Mol. Biochem. Parasit.* 17 (1985) 299–310.

Shehata, et al. Reversed enzyme-linked immunosorbent assay for detection of specific anti-*Plasmodium falciparum* immunoglobulin M antibodies. *Bull. Wld, Hlth. Org.* WHO/MAL/88.1050 (1988) 1–9.

Stone et al. (1990a). Reversed-phase high-performance liquid chromatography for fractionation of enzymatic digests and chemical cleavage products of proteins. *Meth Enzymol* 193: 389–412.

Stone et al. (1990b). Enzymatic digestion of proteins and HPLC peptide isolation in the sub-nanomole range. In: Fini C., Floridi A., Finelli V.N., (ed) LABORATORY METHODOLOGY IN BIOCHEMISTRY. CRC Press, Boca Raton, pp. 181–205.

Tapchaisri, et al. Antibodies against malaria sporozoites in patients with acute uncomplicated malaria and patients with cerebral malaria. *Amer. J. Trop. Med. Hyg.* 34 (1985) 831–836.

Taverne et al. (1990a). Two soluble antigens of *Plasmodium falciparum* induce tumor necrosis factor release from macrophages. *Infect Immun* 58: 2923–2928.

Taverne et al. (1990b). Human and murine macrophages produce TNF in response to soluble antigens of *Plasmodium falciparum*. *Parasite Immunol* 12: 33–43.

Thelu et al. (1985). Purification and immunochemical study of *Plasmodium falciparum* exoantigens. *J Parasitol* 71: 542–546.

Trager W, et al. (1976). Human malaria parasites in continuous culture. *Science* 193: 673–675.

WHO Scientific Group. The use of synthetic antigens for diagnosis of infectious diseases. WHO. *Tech. Rep. Ser.* 784 (1989) 59–64.

Wilson et al. (1969). Antigens associated with *Plasmodium falciparum* infections in man. *Lancet ii:* 201–205.

What is claimed is:

1. An immunogen consisting of peptides having amino acid sequences:

GQDEGEENEG;                  SEQ ID NO:1

GRNGLGANTDQDDQLEDE;          SEQ ID NO:2

DQFFDANPNLFQLLEPVEFDED;   SEQ ID NO:3 and

LVFLVQQPFLFVLWDQNEKFPVFMGVYDP   SEQ ID NO:4 crosslinked by glutaraldehyde.

2. The immunogen of claim 1 where the peptides are crosslinked by treatment with glutaraldehyde followed by Schiff base reduction.

3. An immunogen for inducing antibody production against malarial antigens comprising glutaraldehyde-crosslinked peptides having amino acid sequences:

GQDEGEENEG;   SEQ ID NO:1

GRNGLGANTDQDDQLEDE;   SEQ ID NO:2

DQFFDANPNLFQLLEPVEFDED;   SEQ ID NO:3 and

LVFLVQQPFLFVLWDQNEKFPVFMGVYDP   SEQ ID NO:4 in combination with an immunological adjuvant.

4. The immunogen of claim 3 where the peptides are crosslinked by reaction with glutaraldehyde followed by Schiff base reduction.

* * * * *

UNITED STATES PATENT AND TRADEMARK OFFICE
CERTIFICATE OF CORRECTION

PATENT NO.   :   5,456,911

DATED        :   October 10, 1995

INVENTOR(S)  :   Mark A. James and Sonia Montenegro-James

It is certified that error appears in the above-identified patent and that said Letters Patent is hereby corrected as shown below:

On the title page, item 57, line 5 delete the numeral "3" and insert the numeral --4-- therefor.

Signed and Sealed this

Twenty-sixth Day of December, 1995

Attest:

BRUCE LEHMAN

Attesting Officer                Commissioner of Patents and Trademarks